United States Patent [19]

Meilland, deceased

[11] Patent Number: Plant 6,817

[45] Date of Patent: May 30, 1989

[54] ROSE PLANT — MEIJI KATARSAR VARIETY

[75] Inventor: Marie-Louise Meilland, deceased, late of Antibes, France, by Jean-Pierre Le Naour, legal representative

[73] Assignee: The Conard-Pyle Company, West Grove, Pa.

[21] Appl. No.: 145,395

[22] Filed: Jan. 19, 1988

[51] Int. Cl.[4] ..... A01H 5/00

[52] U.S. Cl. ..... Plt./6

[58] Field of Search ..... Plt. 6

*Primary Examiner*—James R. Feyrer

*Attorney, Agent, or Firm*—Burns, Doane, Swecker & Mathis

[57] ABSTRACT

A new and distinct variety of rose plant of the Miniature Climbing Class is provided which forms in abundance attractive double bright vermilion red blossoms. The climbing and vigorous vegetation of the new variety provides attractive ornamentation for parks and gardens. The blossoms are formed throughout the plant and are particularly long lasting.

1 Drawing Sheet

SUMMARY OF THE INVENTION

The new variety of Miniature Climbing rose plant resulted as a mutation of unknown causation of the Meijikatar variety (U.S. Plant Pat. No. 4,682). The new variety of the present invention was discovered during the selective study of plants formed following the grafting of eyes of such variety. The form and color of the blossoms and foliage of the new variety are identical to those of the Meijikatar variety. However, the vegetation is of the climbing type rather than being dwarf and bushy.

It was found that the new variety of Miniature Climbing rose plant of the present invention possesses the following combination of characteristics:

(a) exhibits a climbing growth habit unlike the bushy growth habit of the Meijikatar variety,
(b) forms double bright vermilion red blossoms, and
(c) forms blossoms throughout the plant which are particularly long lasting.

The new variety well meets the needs of the horticultural industry for many usages. It is particularly well-suited for use as attractive ornamentation for parks and gardens.

The new variety has been found to undergo asexual propagation by a number of routes. The characteristics of the new variety have been found to be strictly transmissible by such asexual propagation from one generation to another.

The new variety has been named the Meiji Katarsar variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety described herein were two years old and observed during November while grafted on *Rosa frobelii* understock and grown in greenhouses at Cannet-des-Maures, Var, France.

DETAILED DESCRIPTION

Figures 1, 2, 3, 4, 5, 6, 7, 8, 9, 10, 11, 12, 13, 14, 15, 16:
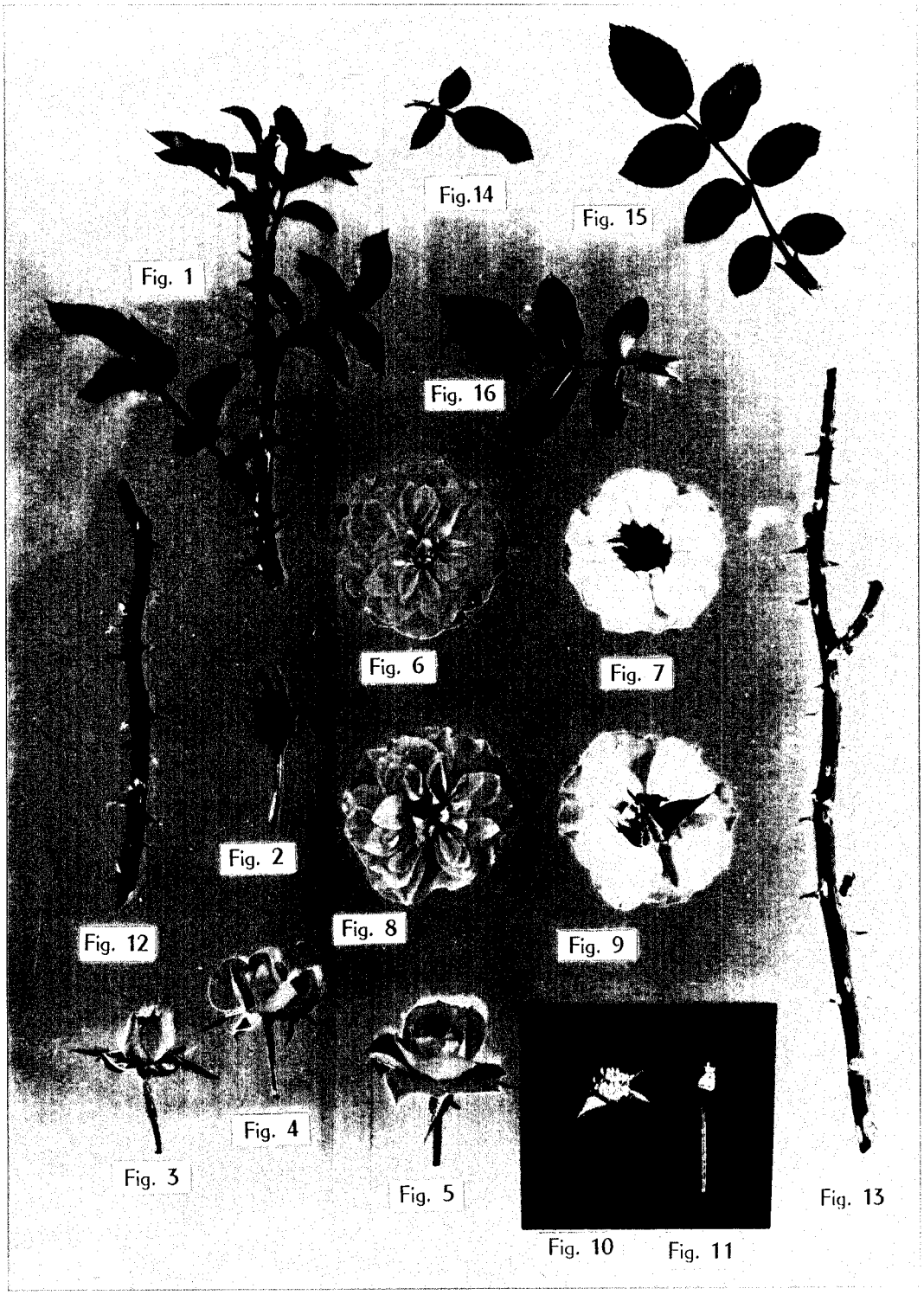
FIG. 1 illustrates a specimen of a young shoot.
FIG. 2 illustrates a specimen of a floral bud before the opening of the sepals.
FIG. 3 illustrates a specimen of a floral bud at the opening of the sepals.
FIG. 4 illustrates a specimen of a floral bud at the opening of the petals.
FIG. 5 illustrates a specimen of a flower in the course of opening.
FIG. 6 illustrates a specimen of a fully open flower — plan view — obverse.
FIG. 7 illustrates a specimen of a fully open flower — plan view — reverse.
FIG. 8 illustrates a specimen of a fully open flower immediately prior to petal drop — plan view — obverse.
FIG. 9 illustrates a specimen of a fully open flower immediately prior to petal drop — plan view — reverse.
FIG. 10 illustrates a specimen of a floral receptacle showing the arrangement of the stamens.
FIG. 11 illustrates a specimen of a floral receptacle showing the arrangement of the pistils (sepals and stamens removed)
FIG. 12 illustrates a specimen of a flowering stem.
FIG. 13 illustrates a specimen of a main branch.
FIG. 14 illustrates a specimen of a leaf with three leaflets — plan view — obverse.
FIG. 15 illustrates a specimen of a leaf with seven leaflets — plan view — obverse.
FIG. 16 illustrates a specimen of a leaf with five leaflets — plan view — reverse.

The chart used in the identification of the colors is that of The Royal Horticultural Society (R.H.S. Colour Chart). The terminology which precedes reference to the chart has been added to indicate the corresponding colors in common terms. The description is based on the observation of two year old specimens of the new variety during November while growing in greenhouses when grafted on *Rosa frobelii* understock at Cannet-des Maures, Var, France.

Class: Climbing Miniature.

Plant:

*Height.*—Approximately 140 to 150 cm. on average.

*Habit.*—Sarmentose.

Branches:

*Color.*—Young stems: light green, Yellow-Green Group 144A, more or less shaded with a reddish tint. Adult wood: bronzed green, Yellow-Green Group 146B.

Leaves:

*Petioles.*—Upper surface: grooved, reddish brown on young foliage and medium green on adult foliage with more or less glandular edges. Under surface: a reddish tint is present on young foliage and the adult foliage is light green, with some small hooked thorns.

*Stipules.*—Adnate, pectinate, narrow and linear.

*Leaflets.*—Number: 3, 5, and 7. Shape: elliptical and slightly lance shaped. Serration: simple and regular. Texture: leathery. General appearance: small and dense foliage with a semi-glossy aspect. Color (young foliage): Upper surface: dark green, Yellow-Green Group 147A. Under surface: medium green, Yellow-Green Group 147B. Color (adult foliage): Upper surface: bronzed green, Yellow-Green Group 146A. Under surface: light green, Yellow-Green Group 147C.

Inflorescence:

*Number of flowers.*—Approximately 1 to 3 per stem.

*Peduncle.*—Straight, rigid, more or less shaded with reddish brown, slightly glandular, bears some small hooked thorns, is sometimes slightly grooved, and its length is approximately 2 to 3 cm. on average.

*Sepals.*—Upper surface: tomentose, greenish, more or less shaded with a reddish tint. Under surface: light green, more or less shaded with red, more or less glandular, and the outside sepals are slightly appendiculated.

*Buds.*—Shape: conical. Length: approximately 1.1 cm. on average when the sepals open. Size: small. Color upon opening: Upper surface: vermilion red, Red Group 44A, bright. Under surface: vermilion red, Red Group 44B.

*Flower.*—Form: initially as a hollow cup and subsequently flattened with visible stamens. Diameter:

approximately 4.8 cm. on average. Color (when opening begins): Upper surface: vermilion red, Red Group 44A, bright. Under surface: vermilion red, Red Group 44C. Color (when blooming): Upper surface: vermilion red, Red Group 44A, bright. Under surface: vermilion red, Red Group 44C. Color (at end of opening): Upper surface: vermilion red, Red Group 44B, bright. Under surface: vermilion red, Red Group 44C. Fragrance: very light. Lasting quality: very long. Petal number: approximately 40 on average. Petal form: rounded, flattened with a small peak on the tip, and folds on itself following a median line. Petal texture: firm. Petal drop: good. Anthers: normal, yellow. Stamen number: approximately 49 on average. Filaments: yellow base and yellow top which is slightly colored with fushsine. Pistil number: approximately 36 on average. Stigmas: normal, yellowish in coloration. Styles: free, straw colored with a fushsine top, more or less twisted and tomentose, of irregular heights. Receptacle: light green, more or less shaded with reddish brown at the dehiscence of the anthers, and in longitudinal section it is narrow and funnel shaped.

Development:

*Vegetation.*—Vigorous.

*Blooming.*—Abundant from the bottom to the top of the plant.

*Aptitude to bear fruit.*—Weak.

*Resistance to frost.*—Normal.

*Resistance to disease.*—Very good.

It is claimed:

1. A new and distinct variety of Miniature Climbing rose plant characterized by the following combination of characteristics:

(a) exhibits a climbing growth habit unlike the bushy growth habit of the Meijikatar variety, (b) forms double bright vermilion red blossoms, and (c) forms blossoms throughout the plant which are particularly long lasting;

substantially as herein shown and described, together with the parts thereof.

* * * * *